US007604118B2

(12) United States Patent
Iio et al.

(10) Patent No.: US 7,604,118 B2
(45) Date of Patent: Oct. 20, 2009

(54) PUNCTURE NEEDLE CARTRIDGE AND LANCET FOR BLOOD COLLECTION

(75) Inventors: Toshiaki Iio, Saijyo (JP); Yoshinori Amano, Saijyo (JP); Koya Kurokawa, Saijyo (JP); Noriyuki Shinohara, Niihama (JP)

(73) Assignee: Panasonic Corporation, Osaka (JP)

( * ) Notice: Subject to any disclaimer, the term of this patent is extended or adjusted under 35 U.S.C. 154(b) by 676 days.

(21) Appl. No.: 11/010,475

(22) Filed: Dec. 14, 2004

(65) Prior Publication Data

US 2005/0145520 A1 Jul. 7, 2005

(30) Foreign Application Priority Data

Dec. 15, 2003 (JP) ............................ 2003-416967
Dec. 17, 2003 (JP) ............................ 2003-419961

(51) Int. Cl.
*A61B 5/151* (2006.01)
*B65D 83/02* (2006.01)
*G07F 11/02* (2006.01)

(52) U.S. Cl. ........................ 206/365; 221/102; 606/181

(58) Field of Classification Search ................. 606/167, 606/181–185; 600/583, 584; 206/359–370; 221/102

See application file for complete search history.

(56) References Cited

U.S. PATENT DOCUMENTS 3,073,307 A * 1/1963 Stevens ...................... 604/192
3,941,244 A * 3/1976 Braginetz ................... 206/360
3,964,482 A * 6/1976 Gerstel et al. ............ 604/890.1
4,794,926 A 1/1989 Munsch et al.
5,361,902 A * 11/1994 Abidin et al. ............... 206/370
5,873,462 A * 2/1999 Nguyen et al. .............. 206/366
6,036,671 A * 3/2000 Frey ........................... 604/110
6,045,567 A 4/2000 Taylor et al.
6,783,537 B1 * 8/2004 Kuhr et al. .................. 606/182
6,880,701 B2 * 4/2005 Bergeron et al. ............ 206/365
6,889,830 B2 * 5/2005 Bergeron et al. ............ 206/365
2003/0223906 A1 * 12/2003 McAllister et al. ............ 422/58

FOREIGN PATENT DOCUMENTS

JP 2002143131 5/2002

* cited by examiner

*Primary Examiner*—Anhtuan T Nguyen
*Assistant Examiner*—Kathleen Sonnett
(74) *Attorney, Agent, or Firm*—Wenderoth, Lind & Ponack, L.L.P.

(57) ABSTRACT

A lancet is pressed against a puncture needle cartridge while fitting a puncture needle loading inlet of the lancet to the axis of a puncture needle on the puncture needle cartridge. In order to facilitate the operation, one of plural puncture needles, arranged in parallel, is tilted up from its initial position at a predetermined angle, and the puncture needle is guided into a puncture needle holding rod of the lancet. Simultaneously, the puncture needle is pressed up to a position where the rear end part of the needle pushes the bottom surface of a puncture needle loading chamber of the puncture needle holding rod, whereby the puncture needle is loaded. When discarding a used puncture needle, the puncture needle is inserted into a lancet guide member of the puncture needle cartridge, whereby the puncture needle is reliably captured to be discarded.

10 Claims, 15 Drawing Sheets

PUNCTURE NEEDLE CARTRIDGE AND LANCET FOR BLOOD COLLECTION

FIELD OF THE INVENTION

The present invention relates to a puncture needle cartridge and a lancet for blood collection. More particularly, the invention relates to a lancet for blood collection, which is used for measuring blood sugar or the like, and has a construction for taking out a plurality of puncture needles one after another, and a puncture needle cartridge for the lancet.

BACKGROUND OF THE INVENTION

A diabetic measures blood sugar several times a day by himself/herself. During the measurement, the diabetic must collect a small amount of blood from a fingertip or the like. For this purpose, as shown in FIG. 13, a disposable puncture needle 105 is attached to an instrument called a lancet 101, and a fingertip or arm is punctured with the needle 105, and blood collected from the punctured region is used for measurement.

The common lancet 101 comprises a cylindrical body 130, and a cap 153. The cylindrical body 130 is provided with a first spring 132 for projecting the attached puncture needle 105, a second spring 134 for backing off the projected puncture needle 105, and an injection button 117 for releasing the compressed first spring 132.

The lancet 101 is used as follows. Initially, the cap 153 is removed from the cylindrical body 130, and the puncture needle 105 is attached to the cylindrical body 130, and then the cap 153 is again put on the cylindrical body 130. Then, the first spring 132 is compressed to set the lancet 101 in a state where puncture is possible, and a puncture target pressing surface 136 of the cap 153 is applied to a target to be punctured, such as a fingertip. When the injection button 107 is pushed, the puncture needle 105 is projected to puncture the target. After the puncture, the puncture needle 105 is immediately removed from the fingertip or the like by the second spring 134. Through the above-mentioned operations, blood is collected. It is very dangerous from a hygienic perspective to reuse the once-used puncture needle 105, and therefore, it is necessary to replace the puncture needle 105 with a new one at next use. (Refer to Japanese Published Patent Application No. 2000-237172).

On the other hand, there is a lancet which holds a plurality of puncture needles, and performs puncture using these puncture needles one by one in turn. After the puncture, the puncture needles can be individually removed from the lancet. This lancet utilizes the elasticity of a flat spring attached to the puncture needle as a driving means for reciprocating the puncture needle. (Refer to U.S. Pat. No. 4,794,926).

By the way, the user believes that the many stages of manual operation using the conventional lancet system, i.e., the above-mentioned puncture needle and puncture operation steps, are troublesome. Therefore, the user is apt to use a once-inserted puncture needle several times for puncture and blood collection. It should be avoided for hygienic reasons to use one puncture needle several times, especially, using one puncture needle for two or more persons. Such situation might occur in, for example, a clinic or a hospital, and a case where a child uses the once-used puncture needle by mistake cannot be excluded.

On the other hand, since a puncture needle is manufactured as a single-use needle, the needle tip becomes dull in a short time if it is used several times, and therefore, successive use of the puncture needle causes more pain to the patient. Furthermore, it is feared that the conventional puncture needle cannot be accurately inserted into the conventional lancet. Further, when the puncture needle and the lancet are improperly used, the user might be wounded.

As described above, in the conventional lancet system, there is a danger that the user might be wounded in his fingertip with the used puncture needle when replacing the puncture needle. Further, since the patient measures blood sugar several times a day, replacement of the puncture needle is very troublesome for the patient. Especially, it is a serious program for a patient who is visually handicapped due to complications associated with diabetes.

SUMMARY OF THE INVENTION

The present invention is made to solve the above-described problems and has for its object to provide a lancet needle cartridge and a lancet for blood collection which provide a simple construction and simple operation for blood collection during blood sugar measurement, thereby improving the handleability of puncture needles.

Other objects and advantages of the invention will become apparent from the detailed description that follows. The detailed description and specific embodiments described are provided only for illustration since various additions and modifications within the scope of the invention will be apparent to those of skill in the art from the detailed description.

According to a first aspect of the present invention, there is provided a puncture needle cartridge, wherein a plurality of puncture needles, each being integrally formed by plastic molding, are arranged in a line on a single substrate, with front ends thereof being integrally plastic-molded with the substrate. Rear ends of the respective puncture needles are open-terminated. Therefore, when puncturing a surface of a living body using a puncture needle, the puncture operation is carried out without exposing the puncture needle at every puncture, and the puncture needles can be continuously loaded on a lancet body.

According to a second aspect of the present invention, in the puncture needle cartridge according to the first aspect, the substrate has a side surface in its longitudinal direction on which the plural puncture needles are arranged in parallel. Therefore, when puncturing a surface of a living body using a puncture needle, the puncture operation is carried out without exposing the puncture needle at every puncture, and the puncture needles can be continuously loaded on a lancet body.

According to a third aspect of the present invention, in the puncture needle cartridge according to the first aspect, the plural puncture needles are independent of one another; and the front ends of the respective puncture needles are connected to the substrate with flexibility so that one of the puncture needles, which are arranged in parallel within one plane, can be tilted downward or upward to a state where the puncture needle intersects the plane. Since the puncture needles are tilted up one by one, the puncture needles can be easily set one by one into a predetermined position without being bothered by the adjacent puncture needles.

According to a fourth aspect of the present invention, in the puncture needle cartridge according to the first aspect, when each puncture needle is separated from the substrate, a needle portion of the puncture needle is exposed, and a cap which has covered the puncture needle remains integrally-connected to the substrate. Since, after a puncture needle is removed, caps of adjacent puncture needles are all integrated with each other, dispersion of the caps to be wastes is prevented, and the volume of wastes can be made compact.

According to a fifth aspect of the present invention, in the puncture needle cartridge according to the first aspect, the substrate has, on a side surface thereof, a mechanism for capturing and holding a used puncture needle. Therefore, the used puncture needle can be easily discarded.

According to a sixth aspect of the present invention, in the puncture needle cartridge according to the fifth aspect, the substrate has the used puncture needle holding mechanism at a side surface that is perpendicular to the side surface on which the plural puncture needles are arranged within one plane. Therefore, the used puncture needle can be easily and accurately discarded.

According to a seventh aspect of the present invention, in the puncture needle cartridge according to the fifth aspect, a lancet that holds a used puncture needle is pressed against the used puncture needle holding mechanism provided at the side surface of the substrate. After the used puncture needle holding mechanism captures the used puncture needle, holding of the used puncture needle by the lancet is released, and the lancet is moved backward, whereby the used puncture needle holding mechanism holds the used puncture needle. Therefore, the used puncture needle can be safely discarded without manually touching it.

According to an eighth aspect of the present invention, in the puncture needle cartridge according to the fifth aspect, when a used puncture needle that is held by the puncture needle holding mechanism provided at the side surface of the substrate is externally pressed by a used puncture needle that is held by the lancet, the previously used puncture needle that is held by the holding mechanism is dropped into a waste box of the puncture needle cartridge to be discarded. Therefore, the puncture operation is carried out without exposing the puncture needle at every puncture, and the puncture needles can be continuously loaded on a lancet body.

According to a ninth aspect of the present invention, in the puncture needle cartridge according to the eighth aspect, an inner bottom of a puncture needle holding rod provided in the lancet, which rod holds the rear end of the puncture needle, has a rotation prevention mechanism that serves as a rotation stop for the rear end of the puncture needle when the puncture needle is twisted to exposes the cap at the front end of the puncture needle. Therefore, it is possible to accurately separate the rear half portion of the puncture needle to hold it with a lancet, by capturing the puncture needle with the lancet and then accurately twisting off a portion of the puncture needle between the needle side and the lancet side.

According to a tenth aspect of the present invention, in the puncture needle cartridge according to the eighth aspect, the puncture needle has, in the center thereof, a stopping concave part for holding the rear part of the puncture needle with puncture needle holding claws of the puncture needle holding mechanism provided in the lancet, and separating the rear part of the puncture needle from the front part thereof. Therefore, the lancet can reliably hold the rear part of the puncture needle and separate the rear part from the front part of the puncture needle.

According to an eleventh aspect of the present invention, in the puncture needle cartridge according to the eighth aspect, the substrate has an insertion slot connected to the waste box through which a used biological data measurement sensor that has been used for measurement of biological data from the collected blood is dropped. Therefore, the volume of waste can be made compact.

According to a twelfth aspect of the present invention, there is provided a blood collection lancet for performing puncture using a puncture needle that is taken out of the puncture needle cartridge according to the first aspect. The lancet body is moved from the rear end side of the puncture needle toward the puncture needle in the direction of the axis of the puncture needle to insert the puncture needle in the lancet and automatically hold the needle by the lancet. The puncture needle is pulled backward to expose the front end of the puncture needle from the puncture needle cap that is integrally molded with the puncture needle cartridge, thereby attaching and holding the puncture needle. Therefore, the puncture needle can be reliably separated and removed by the lancet.

According to a thirteenth aspect of the present invention, there is provided a puncture needle cartridge comprising a bottom case in which a plurality of puncture needles are arranged in parallel, an end of each puncture needle being integrally connected to an inner wall of the bottom case. A slide cover that is slidably provided with respect to the bottom case so as to close an upper opening of the bottom case. The slide cover has a convex portion at an end of a puncture needle support that is integrated with the slide cover and supports the puncture needles from the bottom, which convex portion pushes up the plural puncture needles one by one at a predetermined angle when the slide cover slides along the bottom case. Therefore, when attaching a puncture needle onto a lancet, only a target puncture needle is pushed up, whereby replacement of puncture needles can be safely and easily carried out without being bothered by adjacent puncture needles.

According to a fourteenth aspect of the present invention, in the puncture needle cartridge according to the thirteenth aspect, the bottom case has, at a side surface thereof, a mechanism for capturing and holding a used puncture needle. Therefore, the used puncture needle can be easily discarded.

According to a fifteenth aspect of the present invention, in the puncture needle cartridge according to the fourteenth aspect, the bottom case has the used puncture needle holding mechanism at a side surface that is perpendicular to the side surface on which the plural puncture needles are arranged within one plane. Therefore, the used puncture needle can be easily and accurately discarded.

According to a sixteenth aspect of the present invention, in the puncture needle cartridge according to the fifteenth aspect, a lancet that holds a used puncture needle is pressed against the used puncture needle holding mechanism provided at the side surface of the substrate. After the used puncture needle holding mechanism captures the used puncture needle, holding of the used puncture needle by the lancet is released, and the lancet is moved backward, whereby the used puncture needle holding mechanism holds the used puncture needle. Therefore, the used puncture needle can be safely discarded without manually touching it.

According to a seventeenth aspect of the present invention, in the puncture needle cartridge according to the fifteenth aspect, when a used puncture needle that is held by the puncture needle holding mechanism provided at the side surface of the substrate is externally pressed by a used puncture needle that is held by the lancet, the previously used puncture needle that is held by the holding mechanism is dropped into a waste box of the puncture needle cartridge to be discarded. Therefore, the puncture operation is carried out without exposing the puncture needle at every puncture, and the puncture needles can be continuously loaded on a lancet body.

According to an eighteenth aspect of the present invention, in the puncture needle cartridge according to the seventeenth aspect, the bottom case has an insertion slot connected to the waste box through which a used biological data measurement sensor that has been used for measurement of biological data from the collected blood is dropped. Therefore, the volume of waste can be made compact.

According to a nineteenth aspect of the present invention, in the puncture needle cartridge according to the seventeenth aspect, the bottom case and the plural puncture needles are integrally plastic-molded, and a junction between them has flexibility. Therefore, the puncture needle can be reliably separated and removed by a lancet.

As described above, according to the present invention, a blood collecting operation during measurement of blood sugar can be carried out safely with a simple construction and a single operation. Particularly, the conventional puncture operation is very dangerous because a cap at the tip of a puncture needle is removed directly with hands to attach the puncture needle to a lancet every time measurement of blood sugar is carried out. Further, after the measurement is completed, the cap is put on the tip of the puncture needle to discard the needle. In the present invention, the above-mentioned operation is dispensed with. That is, attachment of a puncture needle onto a lancet can be carried out easily and safely. Further, discarding of a used puncture needle can also be carried out safely, and moreover, a biological data measurement sensor that has been used for obtaining biological data from the blood collected by the puncture needle can be easily and safely discarded.

BRIEF DESCRIPTION OF THE DRAWINGS

FIG. 2(*b*) is an upper cross-sectional view illustrating the inner structure of the lancet according to the first embodiment.

FIG. 4(*b*) is a diagram illustrating a method of loading a puncture needle from the puncture needle cartridge according to the first embodiment.

FIG. 4(*c*) is a diagram illustrating a method of loading a puncture needle from the puncture needle cartridge according to the first embodiment.

FIG. 4(*d*) is an external perspective view illustrating a method of loading a puncture needle from the puncture needle cartridge according to the first embodiment.

FIG. 5(*b*) is a diagram illustrating a method of operating the lancet for the puncture needle cartridge for preparation for puncture according to the first embodiment.

FIG. 5(*c*) is a diagram illustrating a method of operating the lancet for the puncture needle cartridge for preparation for puncture according to the first embodiment.

FIG. 6(*b*) is a diagram illustrating an operation for discarding a puncture needle of the lancet for the puncture needle cartridge according to the first embodiment.

FIG. 10(*b*) is a diagram for explaining the operation of the puncture needle cartridge according to the second embodiment.

FIG. 10(*c*) is a diagram for explaining the operation of the puncture needle cartridge according to the second embodiment.

FIG. 10(*d*) is a diagram for explaining the operation of the puncture needle cartridge according to the second embodiment.

FIG. 10(*e*) is a diagram for explaining the operation of the puncture needle cartridge according to the second embodiment.

FIG. 11(*b*) is a diagram for explaining a method of attaching a puncture needle that is held by the puncture needle cartridge to the lancet according to the second embodiment.

FIG. 11(*c*) is a diagram for explaining a method of attaching a puncture needle that is held by the puncture needle cartridge to the lancet according to the second embodiment.

DETAILED DESCRIPTION OF THE PREFERRED EMBODIMENTS

Hereinafter, embodiments of the present invention will be described with reference to the drawings.

Embodiment 1

Figure 1:
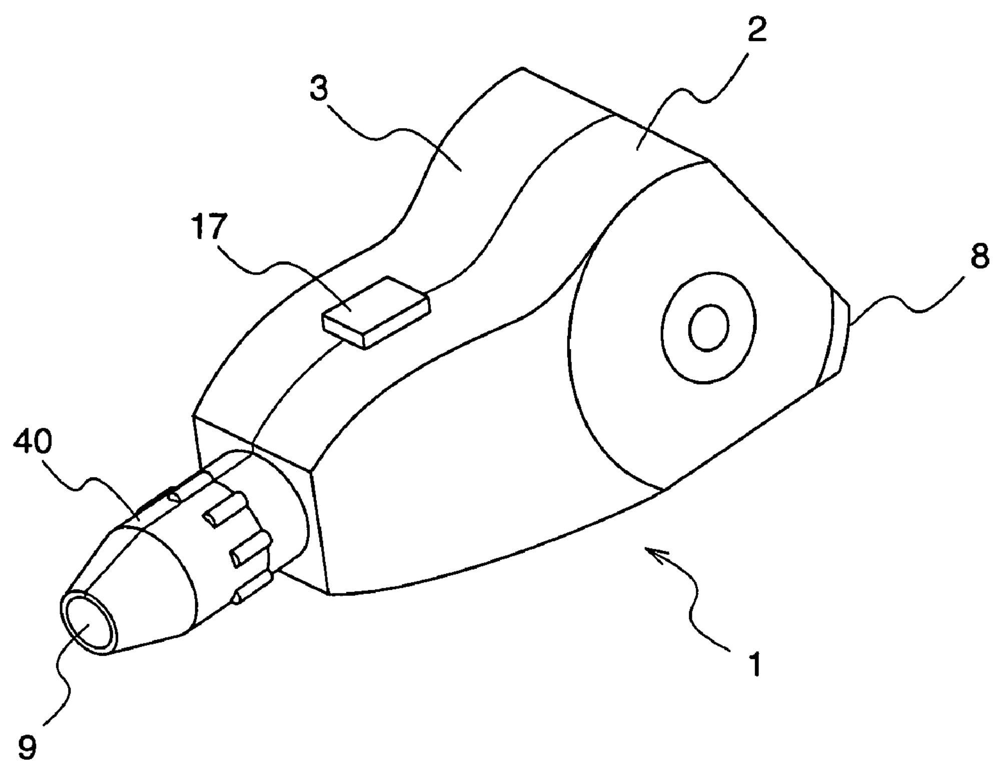
FIG. 1 is an external perspective view of a lancet for blood collection according to a first embodiment of the present invention.
Figure 2A:
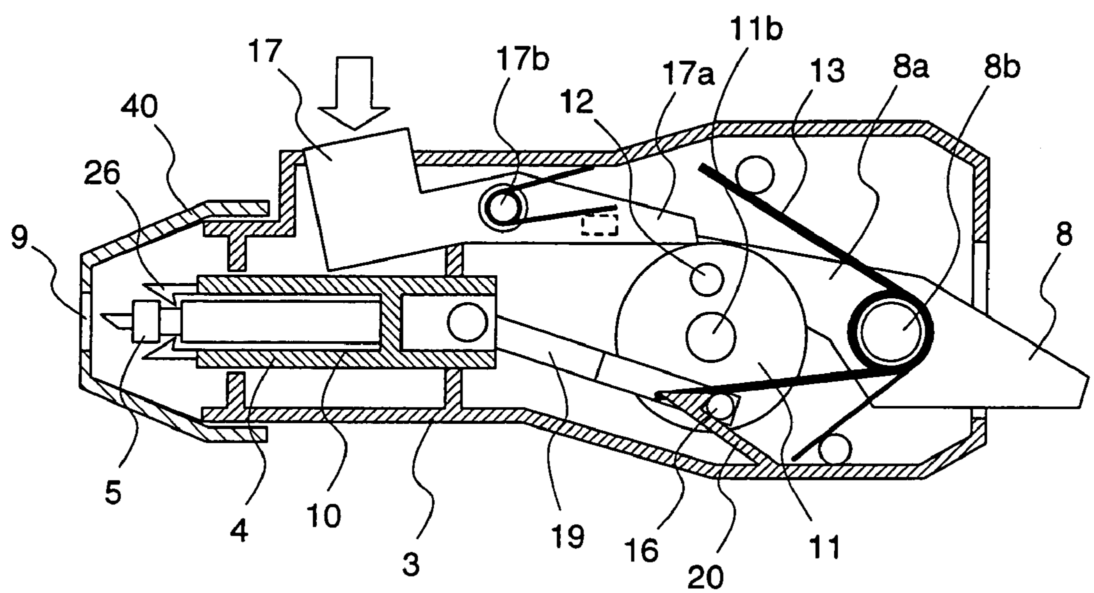
FIG. 2(*a*) is a lateral cross-sectional view illustrating the inner structure of the lancet according to the first embodiment.
Figure 2B:
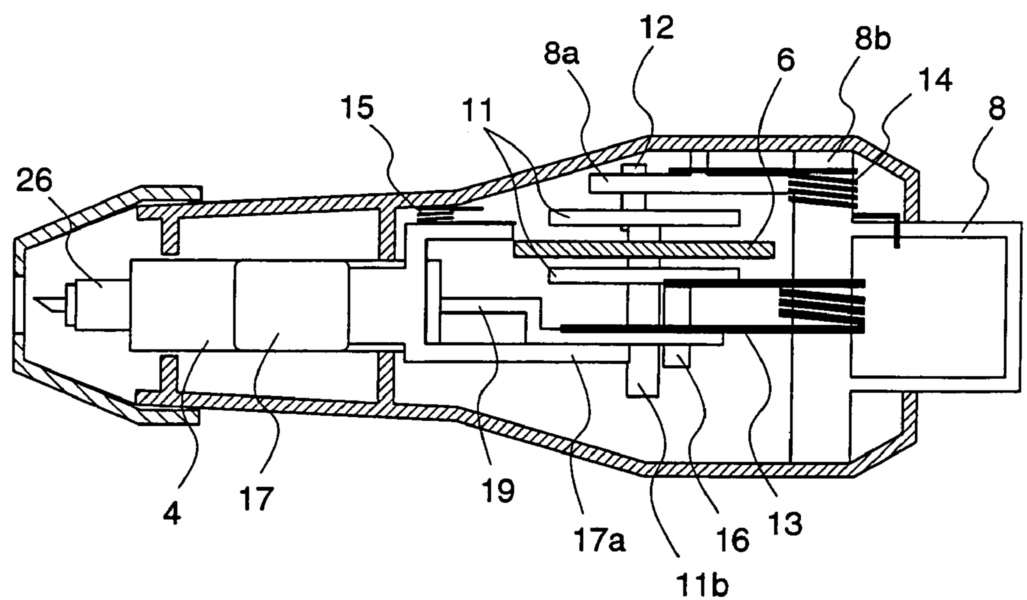
Figure 3:
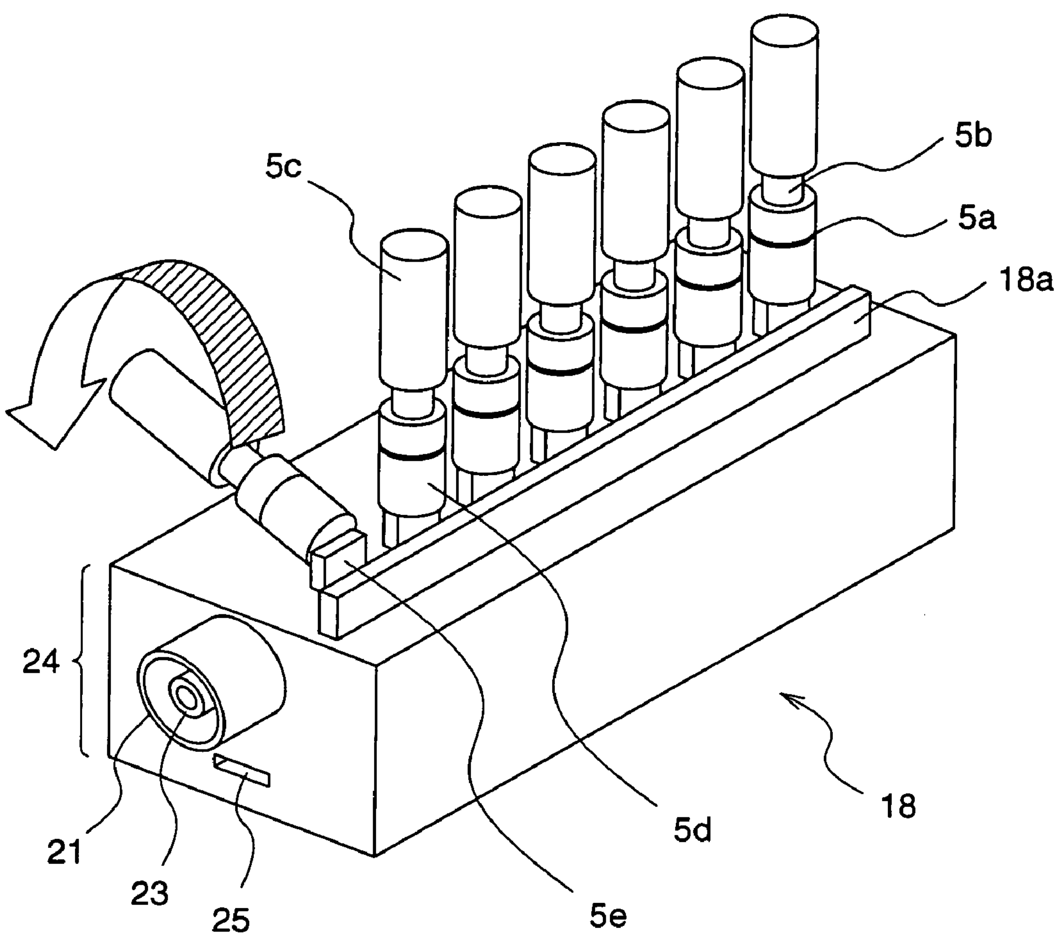
FIG. 3 is a perspective view illustrating a puncture needle cartridge in use according to the first embodiment.
Figure 4A:
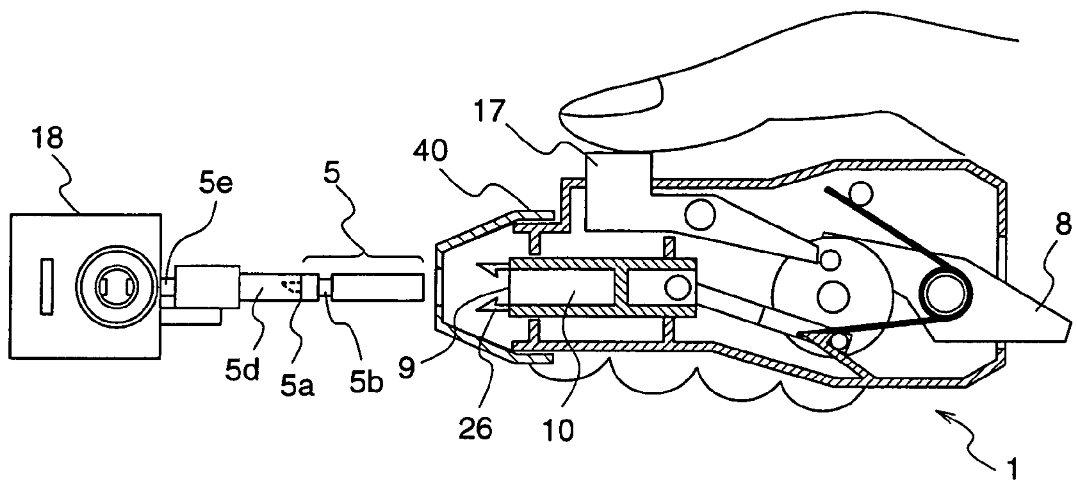
FIG. 4(*a*) is a diagram illustrating a method of loading a puncture needle from the puncture needle cartridge according to the first embodiment.
Figure 4B:
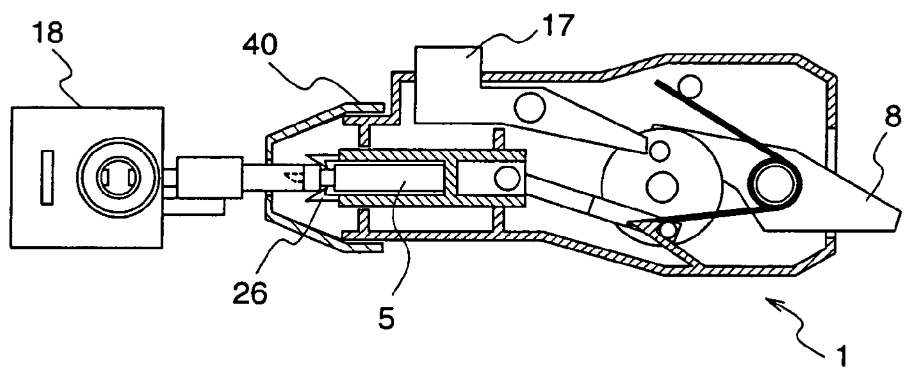
Figure 4C:
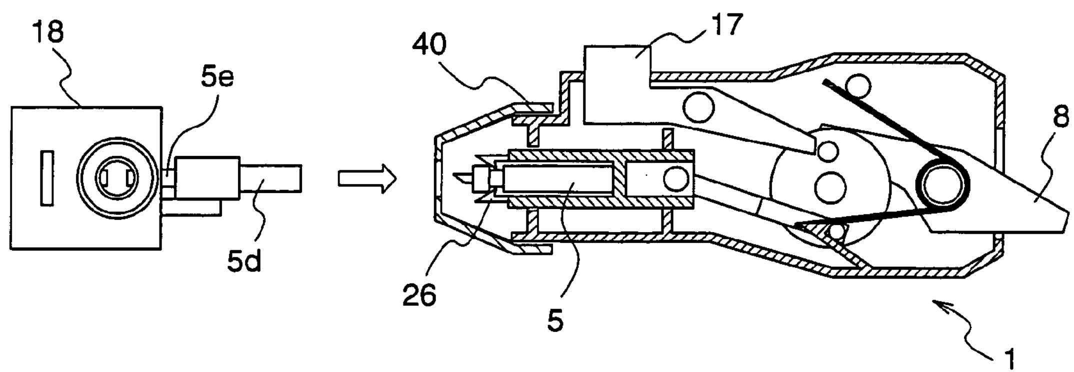
Figure 4D:
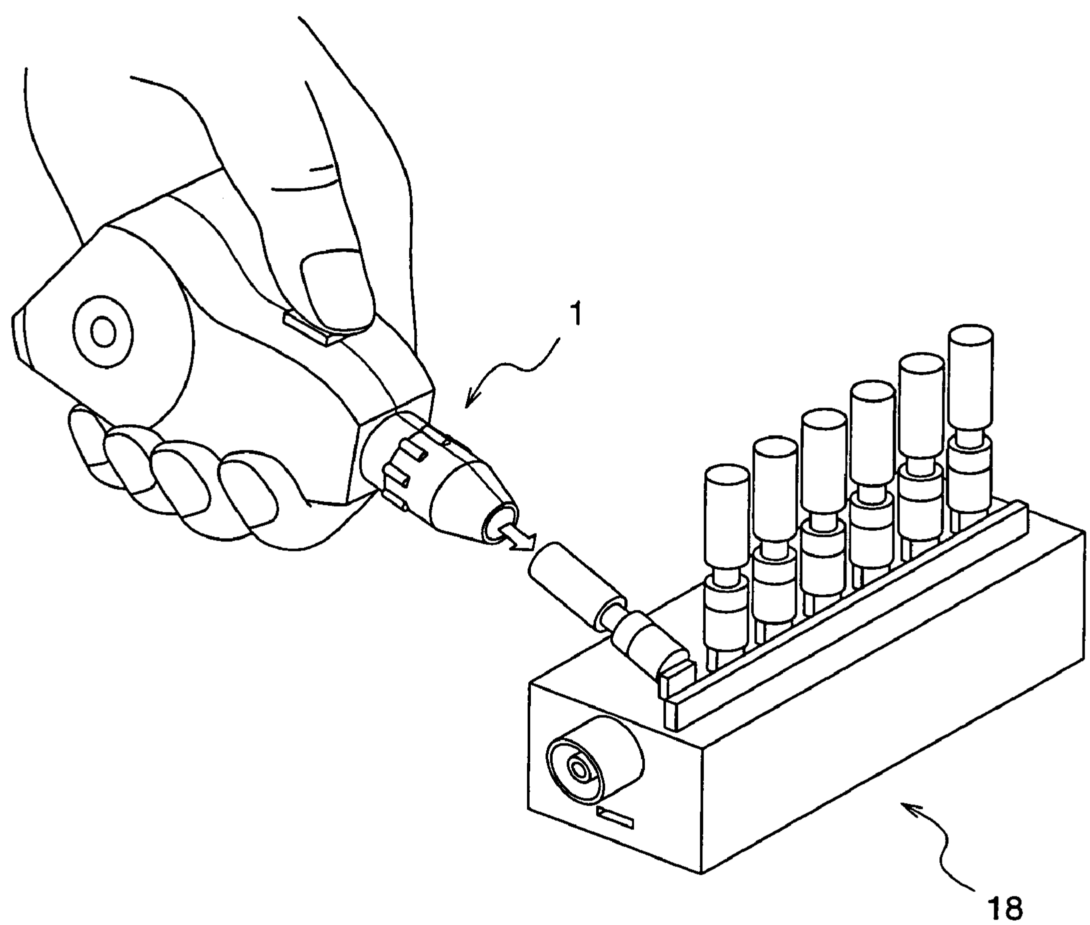

FIG. 1 is an external perspective view of a lancet for blood collection according to a first embodiment of the present invention, FIGS. 2(*a*) and 2(*b*) are cross-sectional views illustrating the internal structure of the lancet, and FIG. 3 is an external perspective view of a puncture needle cartridge to be used for the lancet. The lancet for blood collection and the puncture needle cartridge are used for collecting a small amount of blood for measurement of blood sugar or the like. Further, FIGS. 4(*a*)-4(*c*) are diagrams for explaining the operation of setting a puncture needle onto the lancet body.

With reference to FIG. 1 and FIGS. 2(*a*) and 2(*b*), the lancet 1 according to the first embodiment of the invention has a body bottom case 3, a puncture needle holding rod 4 housed in the body bottom case 3, a body cover 2, and a puncture needle setting lever 8. In the puncture needle holding rod 4, a puncture needle 5 is inserted up to a predetermined depth. Further, as shown in FIG. 3, on a puncture needle cartridge or cartridge body 18, a plurality of puncture needles 5 are arranged in a line, and the needles 5 are integrally molded with a frame of the cartridge by one-piece plastic molding.

That is, a frame 18*a* of the puncture needle cartridge 18 is integrally molded with end parts 5*d* of the puncture needles 5 and puncture needle holders 5*e* for holding the puncture needles 5. Each puncture needle 5 has a neck 5*b* between one end 5*d* and the other end 5*c*. A puncture needle separation groove 5*a* is formed in the approximately center of the one end 5*d* of the puncture needle 5. A thin plastic film having a thickness of 1 mm or less (not shown) is formed at the inner bottom of the puncture needle separation groove 5*a*. The one end 5*d* of the puncture needle 5 and the puncture needle holder 5*e* are integrally plastic molded with the frame 18*a* of the puncture needle cartridge 18. A needle itself of the puncture needle 5 is housed in the one end 5*d* of the puncture needle 5.

Hereinafter, a description will be given of the operational procedures for attaching the puncture needle 5 to the lancet 1.

Initially, in the state where the puncture needle setting lever 8 is not set (pulled downward), a puncture needle loading inlet 9 of the lancet 1 is fitted to the axis of the puncture needle 5 on the puncture needle cartridge 18, and the lancet 1 is pushed (FIG. 4(*a*)). At this time, in order to facilitate the operation, as shown in FIGS. 3 and 4(*d*), one of the puncture needles 5 arranged in parallel (the one on the left end in FIG. 4(*d*)) is previously tilted by a predetermined angle from the initial state. In this state, the lancet 1 is pushed to a position where the rear end portion 5*c* of the puncture needle 5 that is guided into the puncture needle holding rod 4 of the lancet 1 presses the bottom of a puncture needle loading chamber 10 of the puncture needle holding rod 4. In this state, the neck (center convex portion) 5*b* of the puncture needle 5 is engaged with puncture needle holding claws 26 that are provided at the inlet of the puncture needle holding rod 4 (FIG. 4(*b*)). In the state where the puncture needle 5 is held in the puncture needle holding rod 4 of the lancet 1, if the user tries to back off the lancet 1 to separate the lancet 1 from the puncture needle cartridge 18, the lancet 1 performs an operation of pulling apart the puncture needle 5 from the puncture needle cartridge 18. In the process of the operation of pulling apart the puncture needle from the cartridge, a force is applied to the thin plastic film, which is provided in the puncture needle separation groove 5*a* of the one end 5*d* of the puncture needle 5, to pull off the thin film, and a force against this pulling force is generated. When the user further applies a force to separate the lancet 1 in addition to the pulling force, the body of the puncture needle 5 including the other end 5*c* and the rear portion of the one end 5*d* of the puncture needle 5 is separated from the body of the puncture needle cartridge 18 (FIG. 4(*c*)).

Figure 5A:
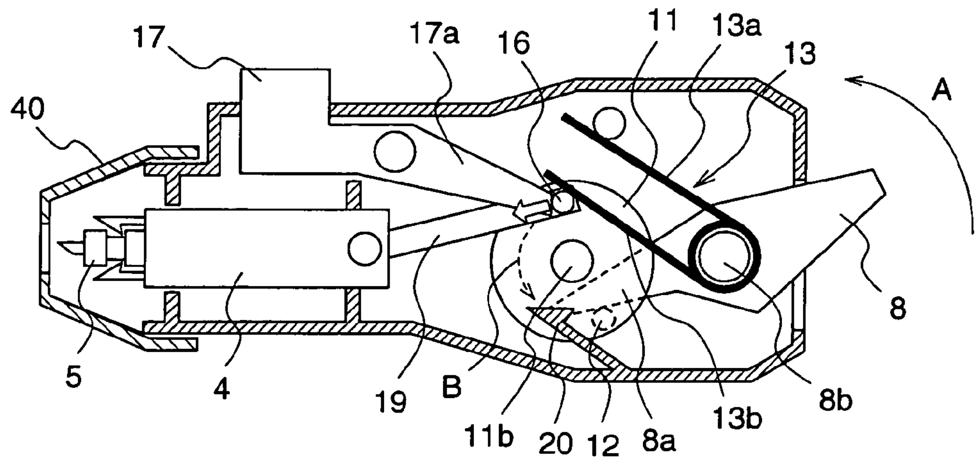
FIG. 5(*a*) is a diagram illustrating a method of operating the blood collection lancet for preparation for puncture according to the first embodiment.
Figure 5B:
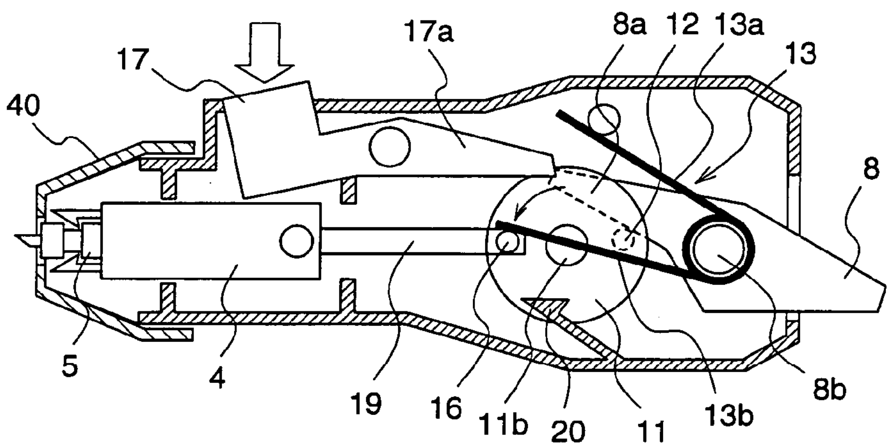
Figure 5C:
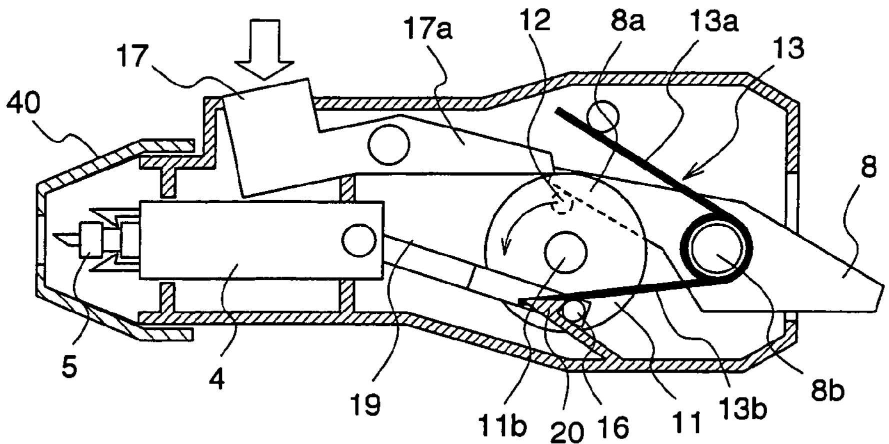

Thereafter, in order to perform puncture from the state shown in FIG. 4(*c*), the puncture needle setting lever 8 is tilted upward by a predetermined angle in the direction indicated by arrow A as shown in FIG. 5(*a*), whereby the lancet 1 is set in a puncture-ready state. Hereinafter, a description will be given of preparation for a puncture operation, and the puncture operation itself.

Initially, a puncture depth adjustment ring 40 provided at the front end of the lancet 1 is rotated about the axis to shift the position of the puncture depth adjustment ring 40 in the axis direction of the lancet 1, whereby a predetermined puncture depth of the puncture needle 5 is set.

Then, the puncture needle 5 is loaded in the puncture needle holding rod 4 of the lancet 1, and thereafter, the puncture needle setting lever 8 is tilted by a predetermined angle in the direction of arrow A, whereby a wheel rotation lever 8*a* on the puncture needle setting lever 8 comes into contact with a set pin 12 on a flywheel to rotate the flywheel 11 in the setting direction (the direction of arrow B in FIG. 5(*a*), i.e., counterclockwise). At this time, with the rotation of the flywheel 11, a wheel engagement pin 16 as a joint between the flywheel 11 and a link 19 presses a left-side portion 13*b* of a flywheel setting spring 13 so that the flywheel setting spring 13 is more compressed. After the flywheel setting spring 13 has passed through the maximum pressed state, the left-side portion 13*b* of the flywheel setting spring 13 becomes approximately parallel to the right-side portion 13*a* of the flywheel 11, and the wheel engagement pin 16 comes into contact with the front end side portion of a wheel engagement pin stop lever portion 17*a* at the front end of the puncture button 17 that is rotatably supported by an external operation, whereby rotation of the flywheel 11 is stopped, and the lancet 1 is in the puncture-ready state.

As described above, while the flywheel 11 is rotated by a predetermined angle from the state of FIG. 4(*c*) to the puncture-ready state shown in FIG. 5(*a*), the puncture needle holding rod 4 coupled to the flywheel 11 is slid in the axis direction of the lancet 1 by the link 19 that converts the rotation of the flywheel 11 into the sliding motion of the puncture needle holding rod 4. During the above operation, the wheel engagement pin 16 on the flywheel 11 and the puncture needle holding rod 4 are coupled with each other by the single link 19, and the flywheel 11 is rotated only in the predetermined direction (counterclockwise) by the puncture needle setting lever 8 as described above. Therefore, the wheel engagement pin 16 rotates, at the beginning, so as to move away from the puncture needle holding rod 4, and the puncture needle holding rod 4 sinks into the body of the lancet 1. Thereafter, the flywheel 11 further rotates, and the end of the wheel engagement pin 16 is stopped by the front end side portion of the wheel engagement pin stop lever portion 17*a* that is the end of the rotatably supported puncture button 17, whereby the flywheel 11 stops and, simultaneously, the motion of the puncture needle holding rod 4 also stops, and the flywheel 11 goes into the state where the force for rotation, which is obtained by the force of the flywheel setting spring 13, is conserved by the puncture button 17 located in the puncture-ready position, and thus setting is completed (FIG. 5(*a*)).

Next, the puncture operation will be described.

Figure 7:
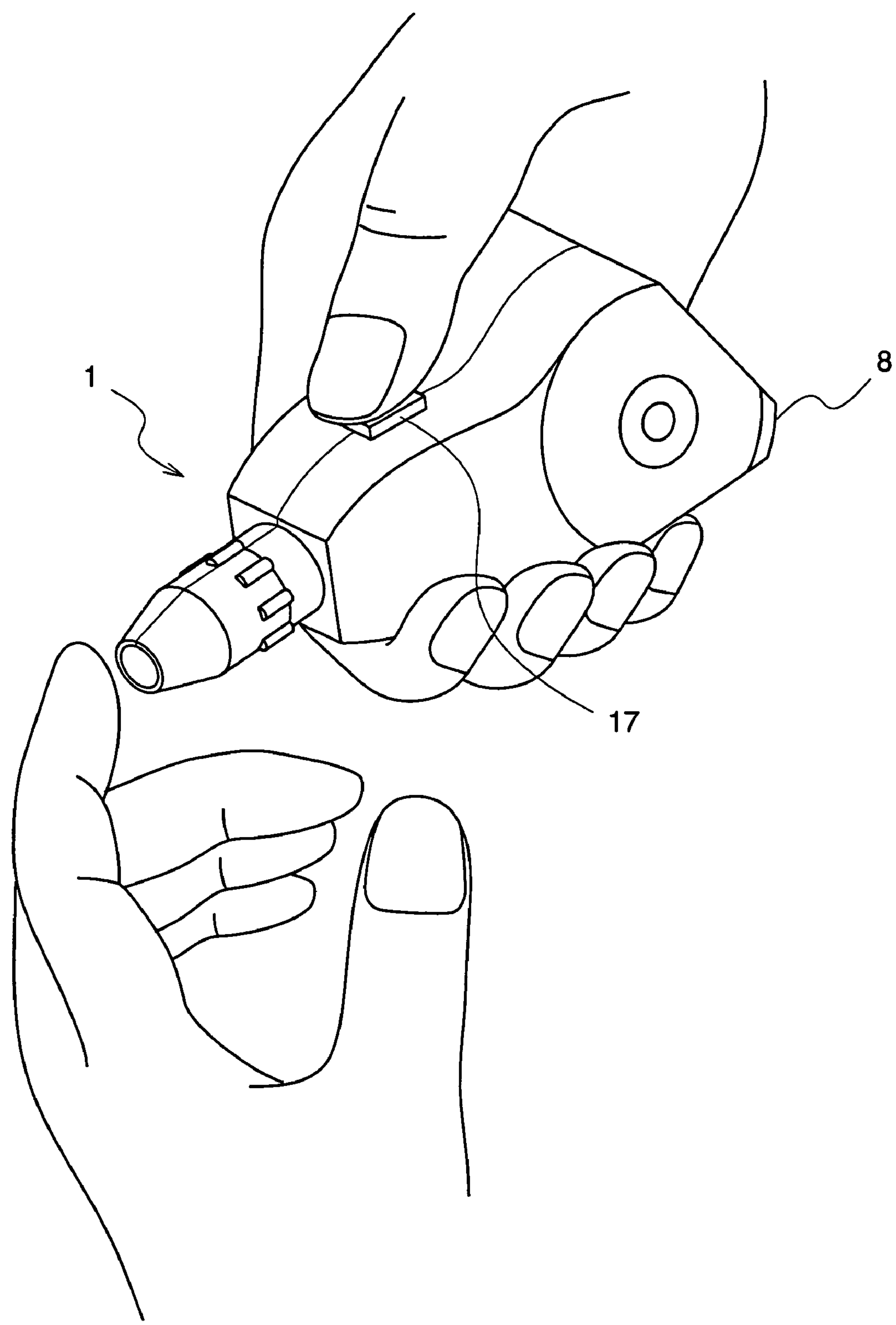
FIG. 7 is a perspective view illustrating a puncture operation by the lancet for the puncture needle cartridge according to the first embodiment.

When the user holds the lancet 1 in the state shown in FIG. 5(*a*) with the hand as shown in FIG. 7 and presses the puncture button 17, a portion of the puncture button 17 on the wheel engagement pin stop lever 17*a* side rotates upward, and the wheel engagement pin stop lever 17*a* pushes the wheel engagement pin 16 to the right in the figure, whereby the wheel engagement pin 16 moves to the right while slightly rotating the flywheel 11 clockwise, and thereby engagement of the wheel engagement pin stop lever 17*a* and the wheel engagement pin 16 is released. As a result, the flywheel 11, which has conserved the rotation force obtained by the force of the flywheel setting spring 13, releases the force at a stroke, whereby the flywheel 11 rotates about the axis in the direction of arrow B (counterclockwise).

At this time, the puncture needle holding rod 4, which is connected to the flywheel 11 by the link 19, linearly moves (slides) outward from the inside of the lancet 1. Thereafter, with the rotation of the flywheel 11, the puncture needle 5 protrudes at its maximum from the lancet 1, i.e., the link 19 is positioned in a straight line in the longitudinal direction of the puncture needle holding rod 4 (FIG. 5(*b*)), and thereafter, the puncture needle 5 returns to the inside of the lancet 1 due to the inertial force of the flywheel 11. During the returning operation, with the force of the flywheel setting spring 13, the wheel engagement pin 16 at the end of the link 19 reaches a position that is most distant from the line connecting the rotation center 8*b* of the puncture needle setting lever 8 and the rotation center 11*b* of the flywheel 11, and the wheel engagement pin 16 attenuates while reciprocating with this position in the center until it stops in this position, and finally, stops. At this time, it is necessary to prevent the puncture needle holding rod 4 from turning back along the direction in which the puncture needle 5 protrudes from the lancet 1. For this purpose, the wheel engagement pin 16 is provided with an anti-inverse rotation claw 20 that is planted on the bottom case 3 so that motion of the wheel engagement pin 16 is not returned to the puncture position, and the engagement between the wheel engagement pin 16 and the anti-inverse rotation claw 20 prevents the flywheel 11 from moving in the inverse rotation direction (FIG. 5(*c*)).

Next, a description will be given of the process of discarding the puncture needle 5 after the puncture operation.

Figure 6A:
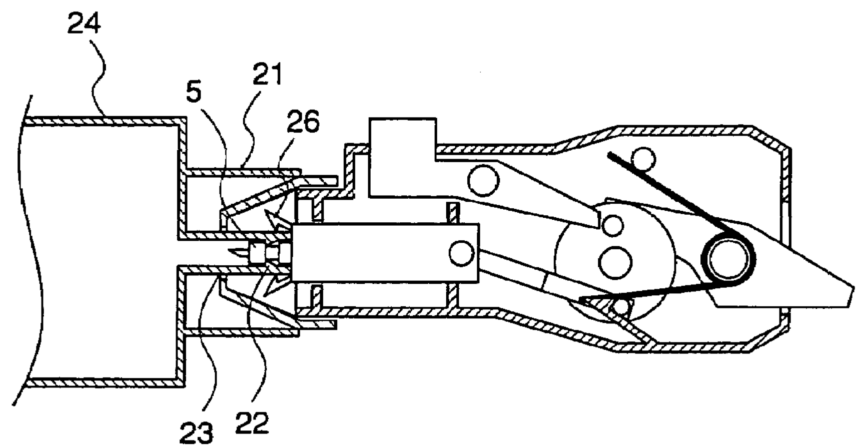
FIG. 6(*a*) is a diagram illustrating an operation for discarding a puncture needle of the lancet for the puncture needle cartridge according to the first embodiment.
Figure 6B:
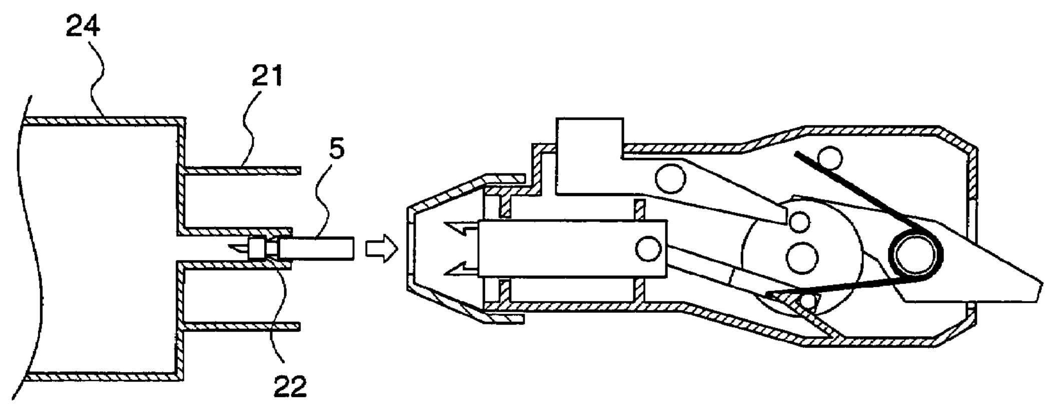

In the state where the above-mentioned puncture operation is completed, the puncture needle loading inlet 9 side of the lancet 1 is inserted into the lancet guiding member 21 of the puncture needle cartridge 18. At this time, the puncture needle pull-out claw 22 at the end of the inner cylindrical member 23 provided in the lancet guide member 21 enters in the neck 5*b* of the puncture needle 5 and, simultaneously, the end of the inner cylindrical member 23 having the puncture needle pull-out claw 22 pushes the puncture needle holding claw 26 at the end of the puncture needle holding rod 4 outward as shown in FIG. 6(*a*), whereby the puncture needle 5 itself is captured in the inner cylindrical member 23 (FIG. 6(*b*)). Thereafter, the lancet 1 is pulled out, whereby the used puncture needle 5 is firmly held in the puncture needle cartridge 18. Thereafter, the previously used puncture needle 5 that is held by the puncture needle cartridge 18 is pushed with a next used puncture needle 5, then held by the lancet 1, whereby the previously used lancet needle 5 held by the cartridge 18 is dropped into a waste box 24 of the puncture needle cartridge 18, and simultaneously, the next used puncture needle 5 is held by the inner cylindrical member 23 of the puncture needle cartridge 18. By repeating this operation one after another, the used puncture needles 5 are successively discarded in the puncture needle cartridge 18. When all of the needles of the cartridge 18 have been used, these needles are discarded in the cartridge 18 or held by the inner cylindrical member 23, and thereafter, the cartridge 18 itself can be discarded.

By performing the discarding operation on the puncture needles 5 continuously, i.e., one after another, the puncture needles 5 can be discarded in the puncture needle cartridge 18.

Furthermore, as shown in FIG. 3, on the side surface of the cartridge body 18 where the lancet guide member 21 exists, there is provided an insertion slot 25 for discarding a used biological data measurement sensor which has performed measurement of the blood collected by the above-mentioned puncture operation using the lancet 1, and the biological data measurement sensor is dropped through the slot 25 into the cartridge 18, whereby the used puncture needles and the used measurement sensors can be discard together after use.

As described above, in the puncture needle cartridge and the lancet for blood collection according to the first embodiment, only one of the plural puncture needles that are held in the cartridge is tilted at an angle different from those of the remaining needles, and the puncture needle is attached to the lancet. Therefore, attachment and replacement of the puncture needle can be carried out easily, safely, and reliably without being bothered by the adjacent needles. Furthermore, when the puncture needle is attached to the lancet, the neck of the puncture needle is held by the puncture needle holding claw, and the puncture needle that is integrally molded with the cartridge is pulled off. Therefore, attachment of the puncture needle can be safely carried out without dropping the needle, in a hygienically favorable state. Moreover, since the used needles and biosensors are collected in the bottom case of the cartridge, the discarded needles and biosensors can be stored together with the cartridge, thereby making the volume of waste compact.

Embodiment 2

Figure 8:
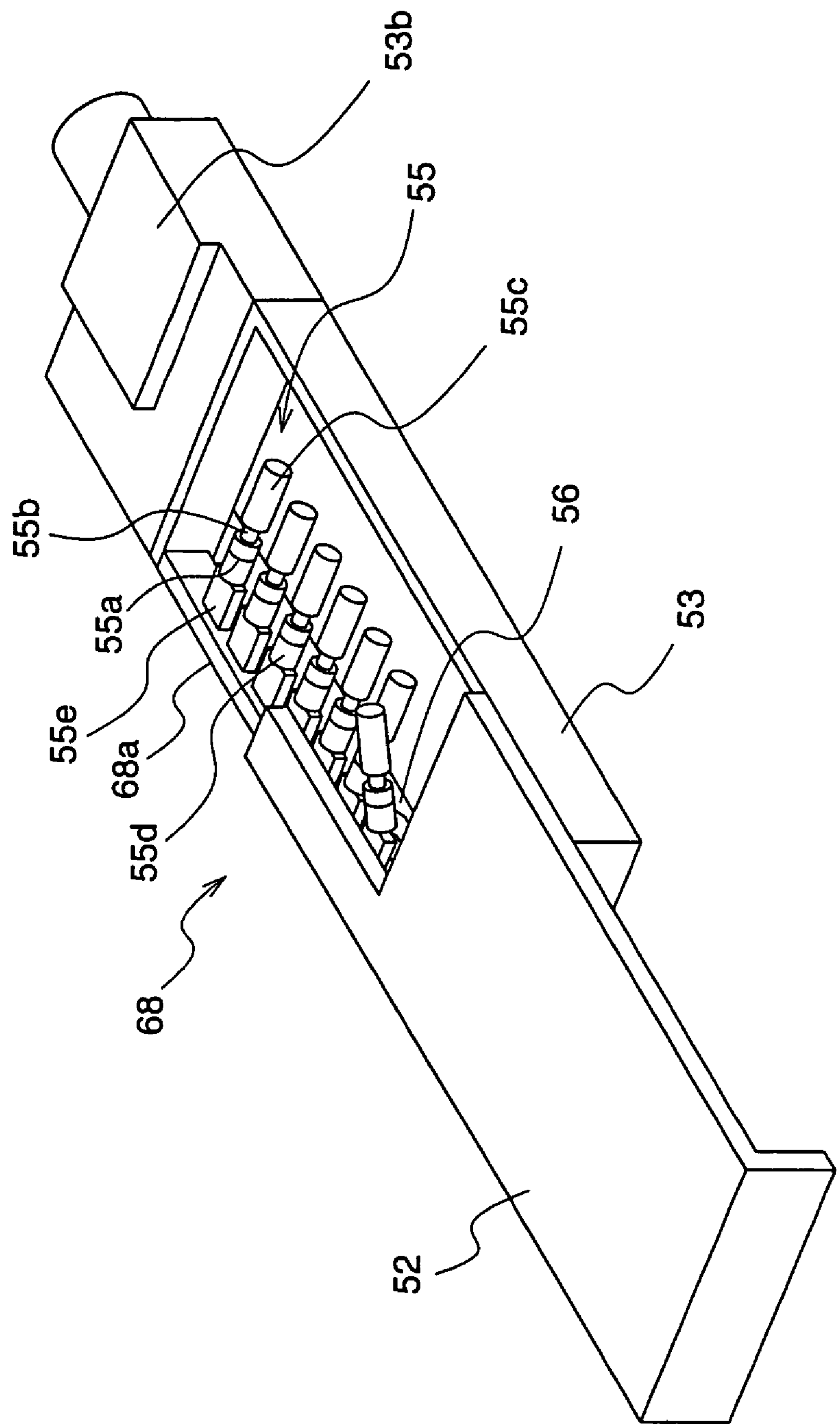
FIG. 8 is an external perspective view of a puncture needle cartridge according to a second embodiment of the present invention.
Figure 9:
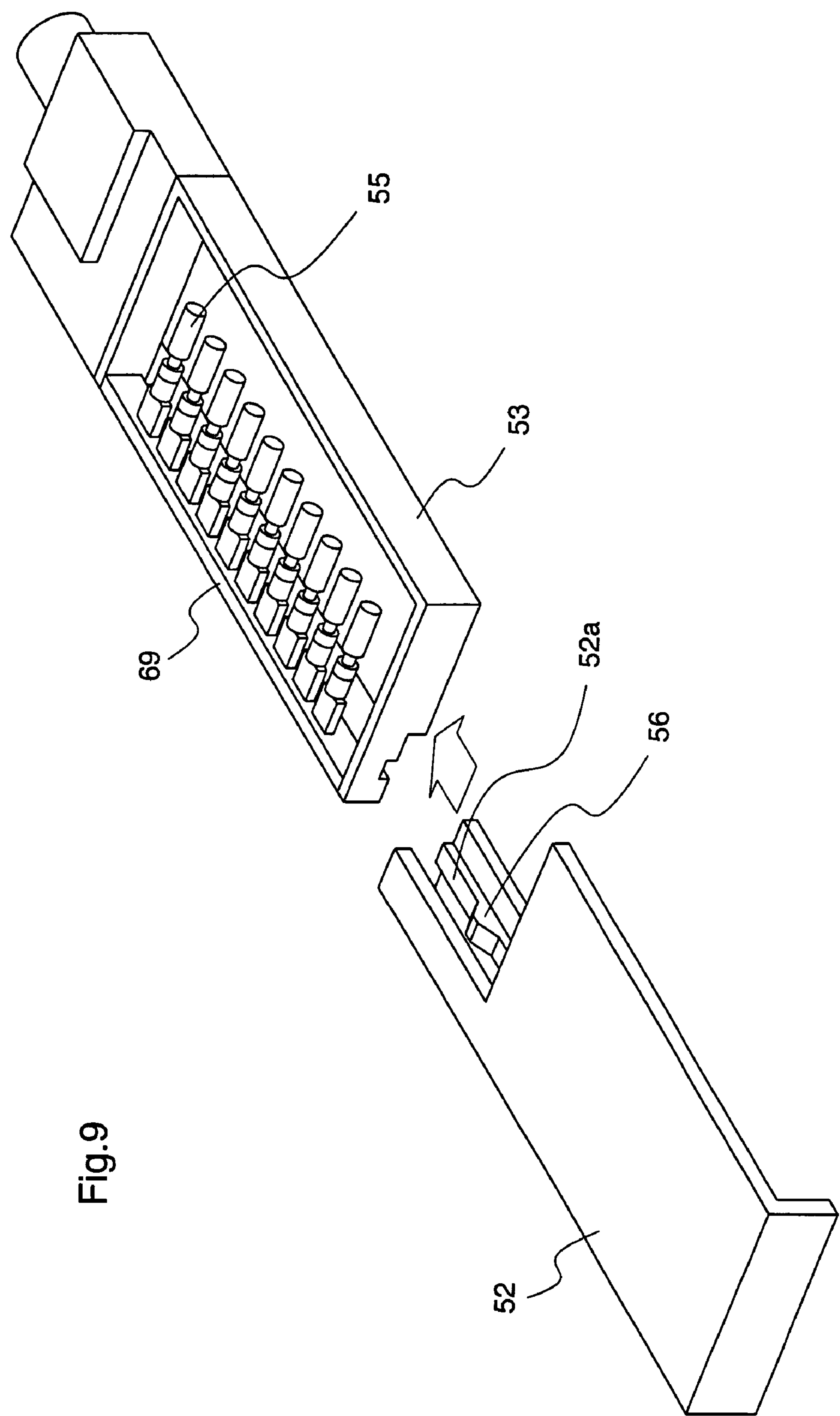
FIG. 9 is an external perspective view illustrating the puncture needle cartridge with a slide cover being removed according to the second embodiment.
Figure 10A:
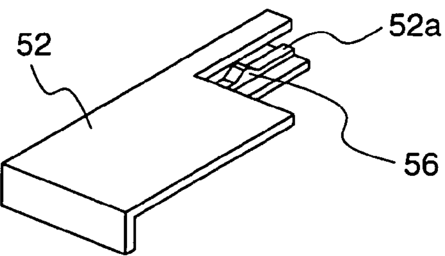
FIG. 10(*a*) is an external perspective view of the slide cover of the puncture needle cartridge according to the second embodiment.
Figure 10B:
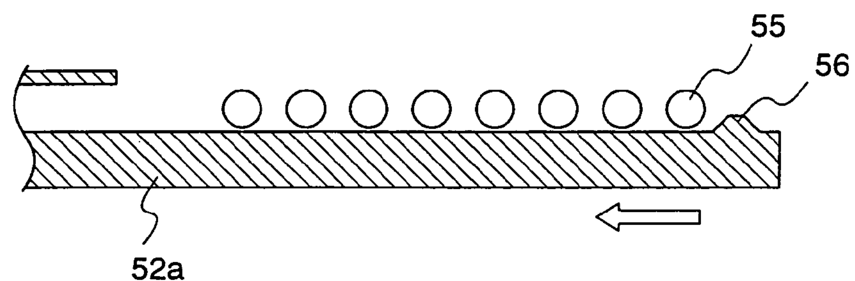
Figure 10C:
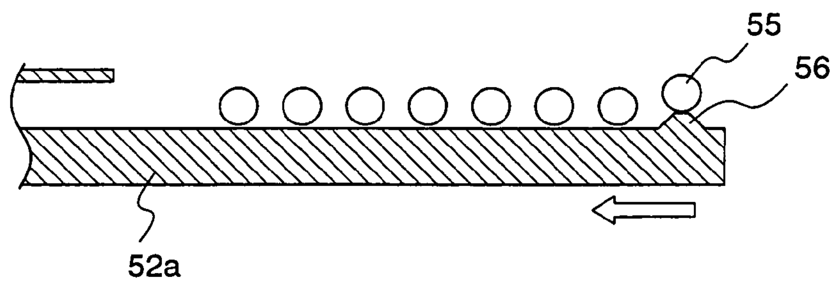
Figure 10D:
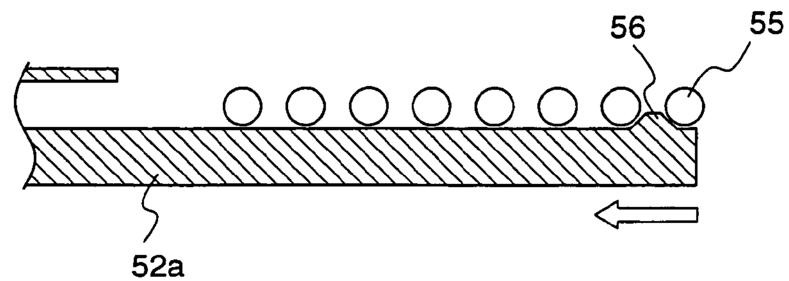
Figure 10E:
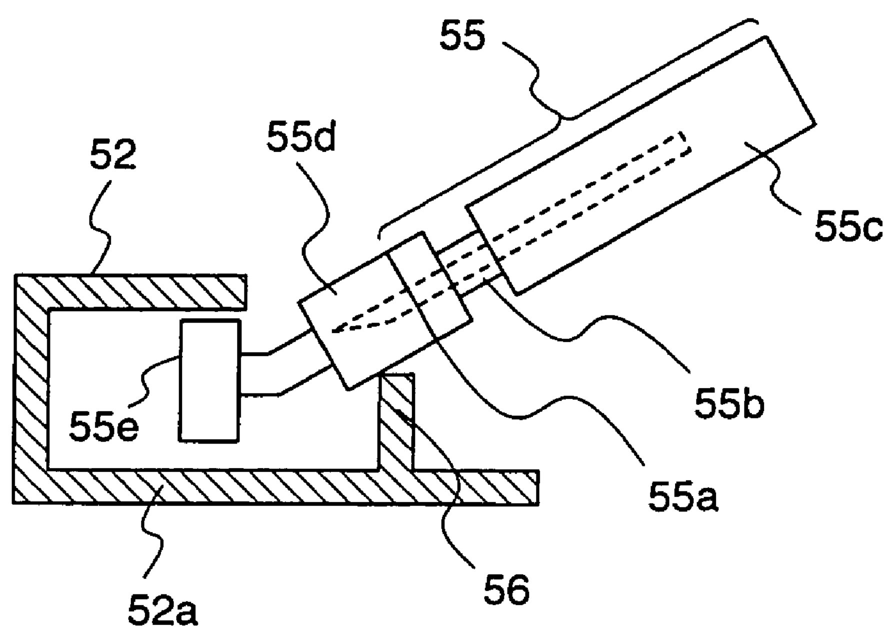
Figure 12:
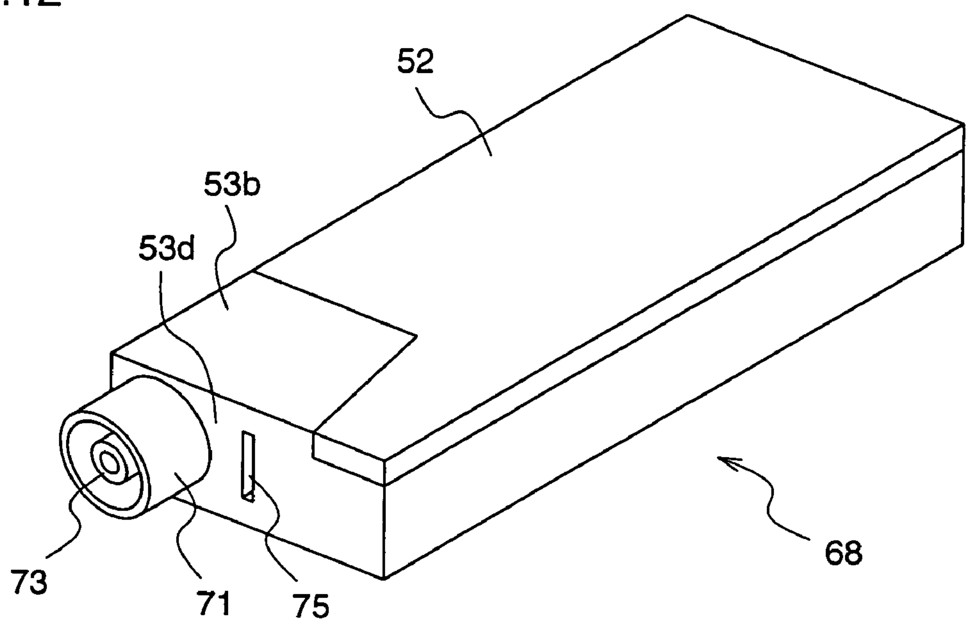
FIG. 12 is an external perspective view illustrating the puncture needle cartridge with the slide cover being closed according to the second embodiment.
Figure 13:
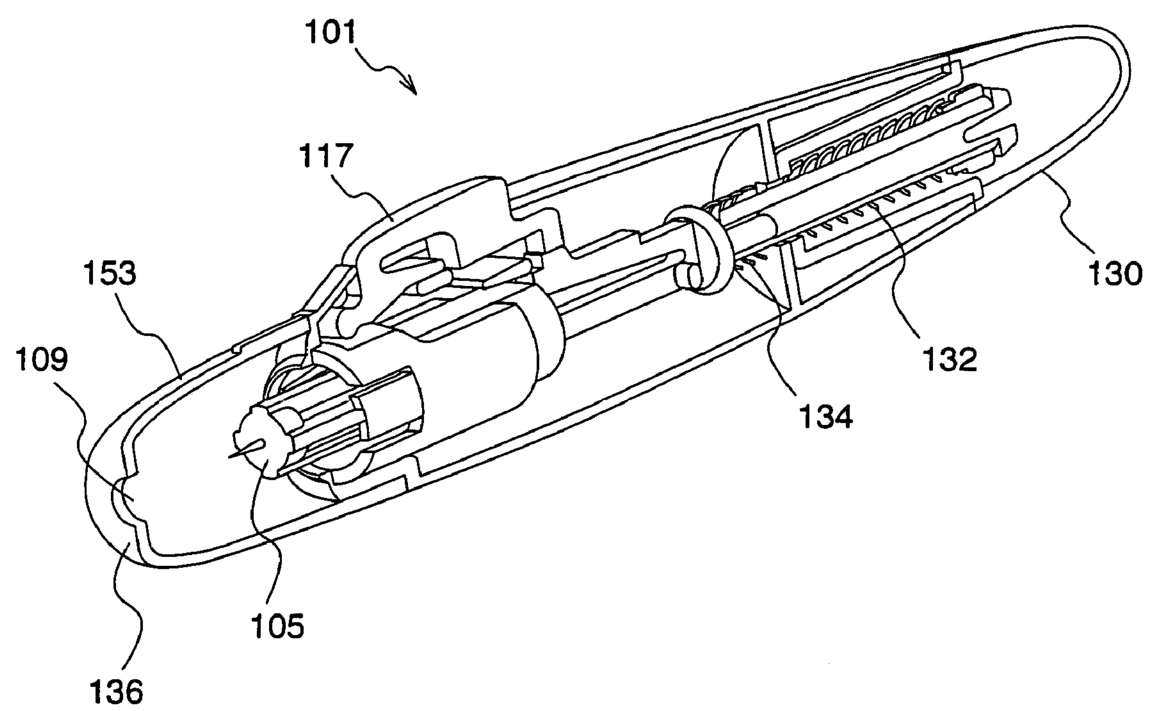
FIG. 13 is a perspective view illustrating the conventional lancet.

FIG. 8 is an external perspective view of a puncture needle cartridge according to a second embodiment of the present invention. FIG. 9 is an external perspective view of the puncture needle cartridge with a slide cover being detached. FIG. 10(*a*) is an external perspective view of the slide cover of the puncture needle cartridge. FIG. 12 is an external perspective view of the puncture needle cartridge with the slide cover being closed.

With reference to FIGS. 8, 9, 10(*a*), and 12, the puncture needle cartridge 68 according to the second embodiment comprises a bottom case 53 in which a plurality of puncture needles 55 are arranged in parallel, with an end of each puncture needle being integrally coupled to an inner wall of the cartridge 68. A slide cover 52 is attached slidably with respect to the bottom case 53 so as to close an upper opening of the bottom case 53.

The bottom case 53 of the puncture needle cartridge 68 has an inner wall 68*a* which is integrally plastic-molded with the respective ends 55*d* of the plural puncture needles 55 arranged in a line in the bottom case 53, and puncture needle holders 55*e* for holding the needles 55. Each puncture needle 55 has a neck 5*b* between one end 55*d* and the other end 55*c*. A puncture needle separation grove 5*a* is formed in the approximately center of the one end 55*d* of the puncture needle 55. A thin plastic film having a thickness of 0.1 mm or less (not shown) is formed at the internal bottom of the puncture needle separation groove 55*a*. The one end 55*d* of each puncture needle 55 and the puncture needle holder 5*e* are integrally plastic-molded with the inner wall 68*a* that is a side wall of the bottom case 53. A needle itself of the puncture needle 55 is housed in the other end 55*d* of the puncture needle 55.

Further, the slide cover 52 has a puncture needle support 52*a*, for supporting the puncture needles 55 from the bottom, integrally molded with the slide cover 55. The puncture needle support 52*a* has a convex portion 56 at a front end, and the convex portion 56 pushes up the plural puncture needles 55 one by one at a predetermined angle when the slide cover 52 slides along the bottom case 53.

Furthermore, a lancet guide member 71 for guiding an end portion of the lancet 51 holding the puncture needle 55, and an inner cylindrical member 73 into which the held puncture needle 55 is to be inserted, which members provide a mechanism for capturing and holding a used puncture needle, are provided on a side surface of the bottom case 53, that is, a front wall 53*d* that is perpendicular to the side surface where the plural puncture needles 55 are arranged in one plane. In the vicinity of the lancet guide member 71, a biosensor insertion slot through which used biosensors are discarded is provided. Further, a waste box 53*b* connected to the inner cylindrical member 73 and the insertion slot 75 are provided inside the front wall 53*d* of the bottom case 53.

Hereinafter, a description will be given of an operation method using the puncture needle cartridge according to the second embodiment, i.e., a method of attaching a puncture needle to the lancet using the cartridge, a method of performing puncture using the lancet with the lancet needle, and a method of discarding the used puncture needle.

Figure 11A:
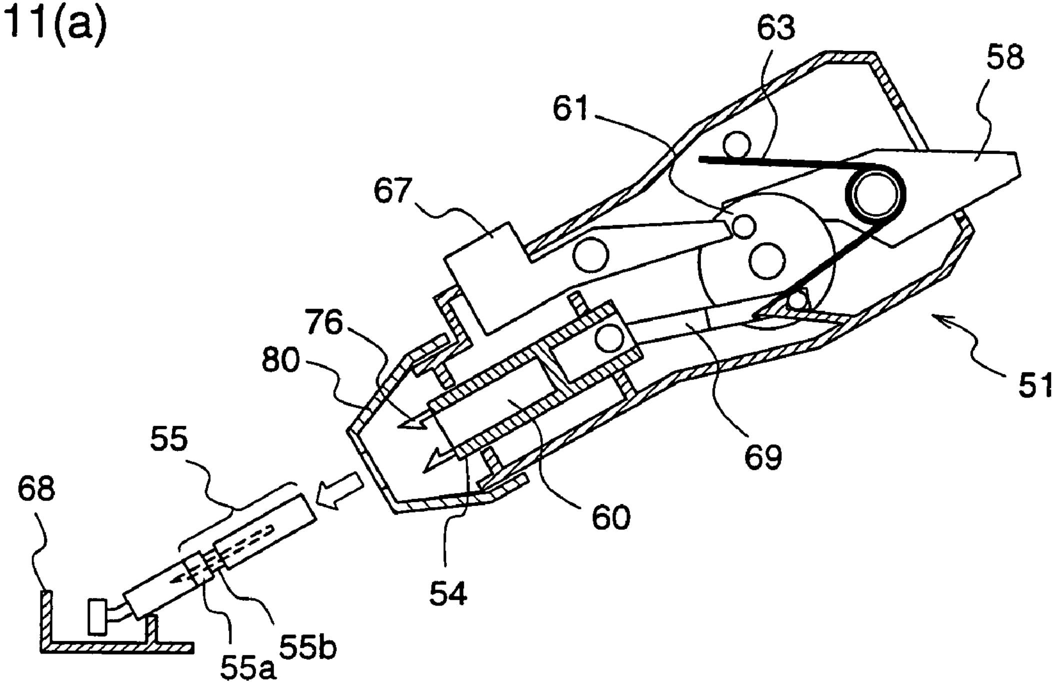
FIG. 11(*a*) is a diagram for explaining a method of attaching a puncture needle that is held by the puncture needle cartridge to the lancet according to the second embodiment.
Figure 11B:
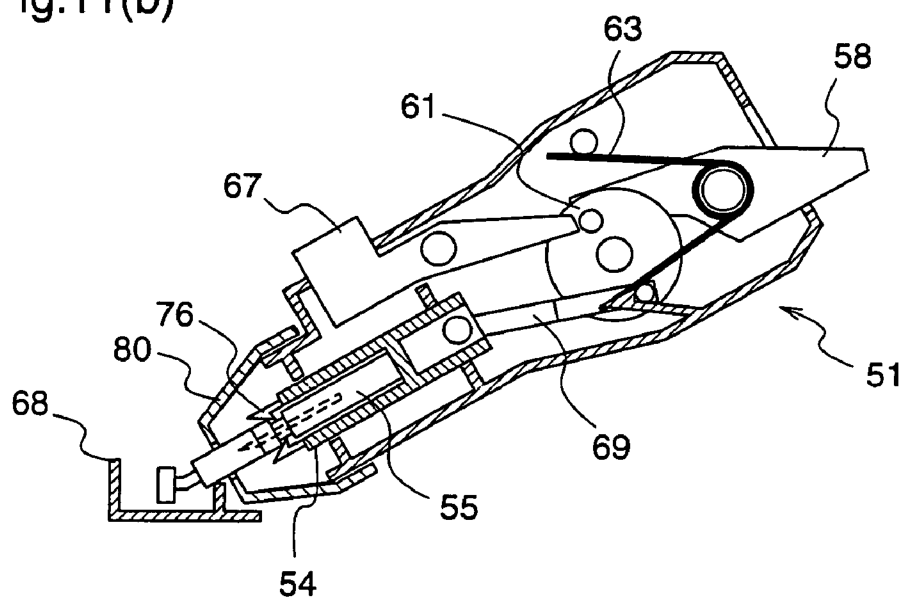
Figure 11C:
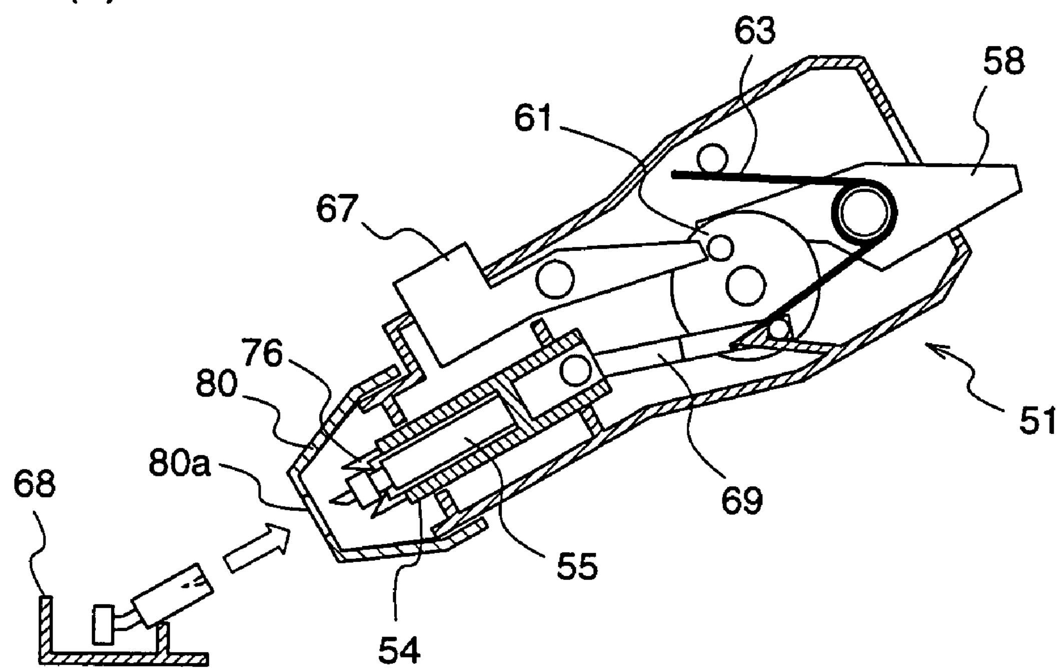

FIGS. 10(*b*)~10(*e*) are schematic diagrams for explaining usage directions for the puncture needle cartridge according to the second embodiment, and FIGS. 11(*a*)~11(*c*) are diagrams for explaining how to attach the puncture needle held by the puncture needle cartridge to the lancet.

The lancet 51 is identical in construction to the lancet 1 according to the first embodiment shown in FIGS. 4(*a*)~4(*c*) and 5(*a*)~5(*c*). As shown in FIG. 11(*a*), the lancet 51 comprises a puncture needle holding rod 54 having a puncture needle loading chamber 60 which is approximately cylindrical in shape, and puncture needle holding claws 76; a flywheel 61 that is rotatably supported by the case of the lancet 51; a flywheel spring 63 for applying a force to rotate the flywheel 61; a connecting link 69 for converting rotation of the flywheel 61 into linear motion of the puncture needle holding rod 54; a puncture needle setting lever 58 for preparing the lancet 51 for puncture operation; a puncture button 67 for starting puncture operation from the puncture-ready state; and a puncture depth adjustment ring 80 for adjusting the depth to which the puncture needle 55 is inserted.

The slide cover 52 of the puncture needle cartridge 68, in the state shown in FIG. 12, is slid to open the aperture of the bottom case so that the plural puncture needles 55 are exposed as shown in FIG. 8 or 9. Thereafter, the slide cover 52 is fitted to the bottom case 53 and slid in the direction that closes the bottom case 53, whereby the ends of the plural puncture needles 55 are pushed up one by one at a predetermined angle by the convex portion 56 which is formed at the front end of the puncture needle support 52*a* that is integrally molded with the slide cover 52 and supports the puncture needles from the bottom, as shown in FIGS. 10(*b*)~10(*d*).

Accordingly, in order to attach the puncture needle to the lancet, the puncture needle 55, one end of which is pushed upward at a predetermined angle, is attached to the lancet 51. More specifically, as shown in FIG. 11(*a*), the center axis of the puncture needle loading chamber 60 of the lancet 51 is aligned with the axis of the puncture needle 55, one end of which is pushed up at a predetermined angle on the puncture needle cartridge 68, and the lancet 51 is pushed against the puncture needle 55, whereby the puncture needle 55 enters into the approximately cylindrical puncture needle loading chamber 60 through an aperture 80*a* of the puncture depth adjustment ring 80. Then, the puncture needle 55 guided into the puncture needle holding rod 54 is press-fitted into the puncture needle loading chamber 60 until the rear end portion 55*c* thereof hits the bottom surface of the puncture needle loading chamber 60. At this time, as shown in FIG. 11(*b*), the neck 55*b* of the puncture needle 55 is engaged with the puncture needle holding claws 76. When the user tries to separate the lancet 51 from the puncture needle cartridge 68, a pulling force is applied to the thin plastic film that is provided in the puncture needle separation groove 55*a* and, simultaneously, a drag against this force occurs in the thin film. When the user further applies a force against this drag to separate the lancet 51, the one end 55*d* of the puncture needle 55 is separated into a front part and a rear part, and removed from the base part 55*e*. Thus, the puncture needle body having the other end 55*c* and the rear part of the one end 55*d* of the puncture needle 55 is separated from the puncture needle cartridge 68, and the lancet 51 holds the puncture needle body as shown in FIG. 11(*c*).

Thereafter, as already described for the first embodiment, the puncture needle setting lever 58 is tilted by a predetermined angle in direction A to perform a puncture preparation operation, and then the puncture button 67 is pressed to protrude the puncture needle holding rod 54 from the inside of the lancet 51 to the outside, thereby enabling a puncture operation.

Further, a method of discarding a used puncture needle 5 after the puncture operation is similar to that described for the first embodiment. More specifically, in this second embodiment, a used puncture needle holding mechanism is provided on a front wall of the bottom cover 53, which is a side surface perpendicular to an inner wall 68*a* of the bottom cover 53 on which the plural puncture needles 55 are arranged within one plane. After the puncture operation, the puncture depth adjustment ring 80 side of the lancet 51 is inserted into the lancet guide member 71 of the lancet needle cartridge 68, whereby the end of the inner cylindrical member 73 pushes the lancet needle holding claws 76 outward, and simultaneously, the lancet needle pull-out claws 72 are engaged with the neck 55*b* of the puncture needle. Thereafter, the lancet 51 is pulled out, whereby the puncture needle 55 is held by the puncture needle holding mechanism provided at the surface of the front wall of the bottom cover 53.

Further, as described for the first embodiment, after one used puncture needle is discarded as described above by the used puncture needle holding mechanism having the lancet guide member 71 and the inner cylindrical member 73, this previously discarded puncture needle 55 is pushed with the next used puncture needle 55 which is held by the lancet 51, whereby the previously used puncture needle 55 is dropped into the waste box 53*b* in the bottom cover 53, and the next used puncture needle 55 is held by the inner cylindrical member 23 at the front surface of the bottom cover 53 to be discarded.

In the vicinity of the used puncture needle holding mechanism comprising the lancet guide member 71 and the inner cylindrical member 73, there is provided an insertion slot 75 connected to the waste box, through which a used biological data measurement sensor which has been used for measuring the blood collected with the puncture needle is dropped. Therefore, the used biological data measurement sensor after the measurement of the biological data from the collected blood can be dropped through the insertion slot 75 to be discarded.

As described above, according to the second embodiment of the present invention, only one of the plural puncture needles that are held in the puncture needle cartridge is tilted upward at a predetermined angle, and the puncture needle is attached to the lancet. Therefore, attachment and replacement of the puncture needle can be carried out easily, safely, and reliably without being bothered by the adjacent needles. Furthermore, when a puncture needle is attached to the lancet, the neck of the puncture needle is held by the puncture needle holding claws, and the puncture needle integrally molded with the cartridge is pulled off. Therefore, attachment of the puncture needle can be safely carried out without dropping the needle, in a hygienically favorable state. Moreover, since the used needles and biosensors are collected in the puncture needle cartridge, the discarded needles and biosensors can be stored together with the cartridge, thereby making the volume of waste compact.

The present invention provides a lancet for blood collection which is used for measuring blood sugar and has a construction for taking out a puncture needle one by one from plural puncture needles, and it is useful for measurement of blood sugar or the like.

What is claimed is:

1. A puncture needle cartridge comprising:

a single substrate;

a plurality of puncture needles, each being integrally formed by plastic molding, arranged in a line on the single substrate, with front ends thereof being integrally plastic-molded with the substrate, and rear ends of the respective puncture needles being free ends;

a waste box for a used puncture needle formed with the single substrate, the waste box being separated from the integrally formed puncture needles; and a puncture needle holding mechanism for capturing and holding a used puncture needle, the puncture needle holding mechanism being disposed on a side surface of the single substrate, wherein each of the respective puncture needles has a stopping part configured to engage puncture needle holding claws of the lancet, the stopping part including a recessed portion, a front stepped portion, and a rear stepped portion, the front stepped portion being formed between a front portion of the respective puncture needle and the recessed portion, the rear stepped portion being formed between a rear portion of the respective puncture needle and the recessed portion, wherein the puncture needle holding mechanism includes a puncture needle pull-out claw for engaging the stopping part of the respective puncture needle so as to hold the respective puncture needle, wherein the puncture needle holding mechanism is configured such that when a used puncture needle held by the puncture needle holding mechanism is externally pressed by another used puncture needle that is held by a lancet, the previously used puncture needle that is held by the puncture needle holding mechanism is dropped into the waste box of the puncture needle cartridge to be discarded, and wherein the puncture needle holding mechanism is configured such that when the lancet that holds a used puncture needle is pressed against the puncture needle holding mechanism, the puncture needle holding mechanism captures the used puncture needle held by the lancet and causes the lancet to release the used puncture needle, and such that when the lancet is drawn away from the puncture needle holding mechanism, the puncture needle holding mechanism holds the used puncture needle.

2. A puncture needle cartridge as defined in claim 1 wherein the puncture needles are independent of one another, and the front ends of the respective puncture needles are connected to the substrate with flexibility so that one of the puncture needles, which are arranged in parallel within one plane, can be tilted downward or upward to a state where the puncture needle intersects the plane.

3. A puncture needle cartridge as defined in claim 1 wherein each of the plurality of puncture needles has a cap at the front end thereof such that when the puncture needle is twisted by an inner bottom of a puncture needle holding rod provided in the lancet, which rod holds the rear end of the puncture needle and prevents rotation through a rotation prevention mechanism that serves as a rotation stop for the rear end of the puncture needle, the cap is exposed at the front end of the puncture needle.

4. A puncture needle cartridge as defined in claim 1 wherein the substrate has an insertion slot connected to the waste box through which a used biological data measurement sensor that has been used for measurement of biological data from the collected blood is dropped.

5. A puncture needle cartridge as defined in claim 1 wherein the puncture needle holding mechanism includes an inner cylindrical member formed on the side surface of the substrate and puncture needle pull-out claws formed at an end of the inner cylindrical member, and the puncture needle holding mechanism is configured to capture and hold the used puncture needle by causing the end of the inner cylindrical member to push the puncture needle holding claws of the lancet outward, and by causing the puncture needle pull-out claws to project into the stopping concave part when the lancet is pressed against the puncture needle holding mechanism.

6. A puncture needle cartridge as defined in claim 1 wherein the puncture needle pull-out claw of the puncture needle holding mechanism is operable to engage the stopping part such that the respective puncture needle is held by the puncture needle holding mechanism until the rear stepped portion is pressed beyond the puncture needle pull-out claw.

7. A puncture needle cartridge comprising:

a substrate;

a plurality of puncture needles arranged in a line on the substrate, with front ends thereof being integrally plastic-molded with the substrate, and rear ends of the respective puncture needles being free ends; and a waste box for a used puncture needle formed with the substrate, the waste box being separated from the integrally formed puncture needles; and a puncture needle holding mechanism for capturing and holding a used puncture needle, the puncture needle holding mechanism being disposed on a side surface of the substrate, the puncture needle holding mechanism including an inner cylinder member, wherein the puncture needle holding mechanism is configured such that when the lancet that holds a used puncture needle is pressed against the puncture needle holding mechanism, the puncture needle holding mechanism captures the used puncture needle held by the lancet and causes the lancet to release the used puncture needle, and such that when the lancet is drawn away from the puncture needle holding mechanism, the puncture needle holding mechanism holds the used puncture needle, wherein the puncture needle holding mechanism is configured such that when a used puncture needle held by the puncture needle holding mechanism is externally pressed by another used puncture needle that is held by a lancet, the previously used puncture needle that is held by the puncture needle holding mechanism is dropped into the waste box to be discarded, and wherein the inner cylinder member of the puncture needle holding mechanism has a length extending outwardly away from an outer surface of said waste box such the previously used puncture needle is not dropped into the waste box to be discarded until the previously used puncture needle is externally pressed.

8. A puncture needle cartridge as defined in claim 7 wherein the plurality of puncture needles are independent of one another, and the front ends of the respective puncture needles are connected to the substrate with flexibility such that the respective puncture needles are tiltable downward or upward.

9. A puncture needle cartridge as defined in claim 7 wherein the substrate has an insertion slot connected to the waste box through which a used biological data measurement sensor that has been used for measurement of biological data from the collected blood is dropped.

10. A puncture needle cartridge as defined in claim 7 wherein the puncture needle holding mechanism includes puncture needle pull-out claws formed at an end of the inner cylindrical member, and the puncture needle holding mechanism is configured to capture and hold the used puncture needle by causing the end of the inner cylindrical member to push puncture needle holding claws of the lancet outward, and by causing the puncture needle pull-out claws to project into the stopping concave part when the lancet is pressed against the puncture needle holding mechanism.

* * * * *